(12) United States Patent
Verma

(10) Patent No.: US 9,729,330 B2
(45) Date of Patent: Aug. 8, 2017

(54) SECURE PAIRING OF EHEALTH DEVICES AND AUTHENTICATION OF DATA USING A GATEWAY DEVICE HAVING SECURED AREA

(71) Applicant: Samsung Electronics Co., Ltd., Gyeonggi-do (KR)

(72) Inventor: Sanjeev Verma, San Jose, CA (US)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 49 days.

(21) Appl. No.: 14/832,763

(22) Filed: Aug. 21, 2015

(65) Prior Publication Data

US 2017/0054563 A1 Feb. 23, 2017

(51) Int. Cl.
*H04L 29/06* (2006.01)
*H04L 9/32* (2006.01)
*A61B 5/00* (2006.01)
*G06F 19/00* (2011.01)
*G06F 21/44* (2013.01)
*G06F 21/62* (2013.01)
*G06Q 50/24* (2012.01)
*H04W 12/06* (2009.01)
*G06F 9/445* (2006.01)
(Continued)

(52) U.S. Cl.
CPC .......... *H04L 9/3263* (2013.01); *A61B 5/0022* (2013.01); *G06F 8/65* (2013.01); *G06F 19/3418* (2013.01); *G06F 21/44* (2013.01); *G06F 21/6245* (2013.01); *G06Q 50/24* (2013.01); *H04L 63/0428* (2013.01); *H04L 63/08* (2013.01); *H04L 63/168* (2013.01); *H04L 67/06* (2013.01); *H04W 12/06* (2013.01); *H04L 67/12* (2013.01); *H04W 12/04* (2013.01)

(58) Field of Classification Search
CPC ...................................... H04L 9/3263
USPC ........................................... 713/153
See application file for complete search history.

(56) References Cited

U.S. PATENT DOCUMENTS 8,621,540 B2 12/2013 Apsangi et al.
8,631,466 B2 1/2014 Cha et al.
(Continued)

FOREIGN PATENT DOCUMENTS

GB 2513976 11/2014

OTHER PUBLICATIONS

Extended European Search Report dated Jul. 20, 2016 in connection with European Application No. 16169255.3, 9 pages.
(Continued)

*Primary Examiner* — Longbit Chai

(57) ABSTRACT

A gateway device, system, and method are presented for securely obtaining health information from a personal medical device. The system installs a gateway application in a gateway device. The gateway application executes in a secure area of the gateway device. The system establishes first secure communications with the gateway application and receives aggregated personal medical device information from the gateway application. The gateway application establishes second secure communications with a personal medical device and receives information from the personal medical device via the second secure communications. The gateway application aggregates information from the personal medical device and send the aggregated information to the system via the first secure communications.

20 Claims, 4 Drawing Sheets

(51) Int. Cl.
   *H04W 12/04*       (2009.01)
   *H04L 29/08*       (2006.01)

(56) References Cited

U.S. PATENT DOCUMENTS

| | | | |
|---|---|---|---|
| 8,684,923 B2* | 4/2014 | Craine | G06F 19/3418 |
| | | | 600/301 |
| 8,751,670 B2* | 6/2014 | Xu | H04L 69/32 |
| | | | 370/401 |
| 8,769,624 B2 | 7/2014 | Cotterill | |
| 9,092,762 B2* | 7/2015 | Jensen | G06Q 10/20 |
| 2007/0165625 A1* | 7/2007 | Eisner | G06F 9/546 |
| | | | 370/389 |
| 2007/0230393 A1 | 10/2007 | Sinha et al. | |
| 2009/0300361 A1* | 12/2009 | Shen | H04L 12/58 |
| | | | 713/171 |
| 2010/0315225 A1 | 12/2010 | Teague | |
| 2011/0145894 A1 | 6/2011 | Garcia Morchon et al. | |
| 2014/0379368 A1 | 12/2014 | Kim et al. | |

OTHER PUBLICATIONS

Wikipedia, "Health (application)", XP055287872, Sep. 17, 2014, retrieved from the Internet: http://en.wikipedia.org/wiki/Health_(application), 4 pages.

* cited by examiner

SECURE PAIRING OF EHEALTH DEVICES AND AUTHENTICATION OF DATA USING A GATEWAY DEVICE HAVING SECURED AREA

TECHNICAL FIELD

The present application relates generally to networks of sensors and/or actuators and, more specifically, to a system and method for secure pairing of eHealth devices and authentication of data using a gateway device having a secured area.

BACKGROUND

Personal medical devices (also known as eHealth devices) provide individualized health data reporting sensors and treatment delivery actuators. Such devices are often attached to or implanted in a patient. A doctor or other health service provider remotely collects current and historical data from a patient's eHealth sensors and delivers treatment instructions to the patient's eHealth actuators.

SUMMARY

In a first embodiment, a gateway device includes a processor, a memory coupled to the processor, and a communications interface coupled to the processor. The gateway device is configured to receive a gateway application from a relying system via the communications interface and execute the gateway application in a secure area of the processor and the memory. The gateway application is configured to establish first secure communications with a personal medical device and establish second secure communications with the relying system. The gateway application is further configured to receive information from the personal medical device via the first secure communications and send aggregated received information to the relying system via the second secure communications.

In a second embodiment, a system for securely obtaining health information from a personal medical device is presented. The system is configured to install a gateway application in a gateway device. The gateway application is adapted to be executed in a secure area of the gateway device. The system is further configured to establish first secure communications with the gateway application and receive aggregated personal medical device information from the gateway application. The gateway application is configured to establish second secure communications with a personal medical device and receive information from the personal medical device via the second secure communications. The gateway application is further configured to aggregate information received from the personal medical device and send the aggregated information to the system via the first secure communications.

In a third embodiment, a method of managing secure data collection from a personal medical device is presented. The method includes receiving from a relying system a gateway application and executing the gateway application in a secure area of a gateway device. The method further includes establishing first secure communications with the personal medical device and establishing second secure communications with the relying system. The method also includes receiving information from the personal medical device via the first secure communications and sending aggregated received information to the relying system via the second secure communications.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
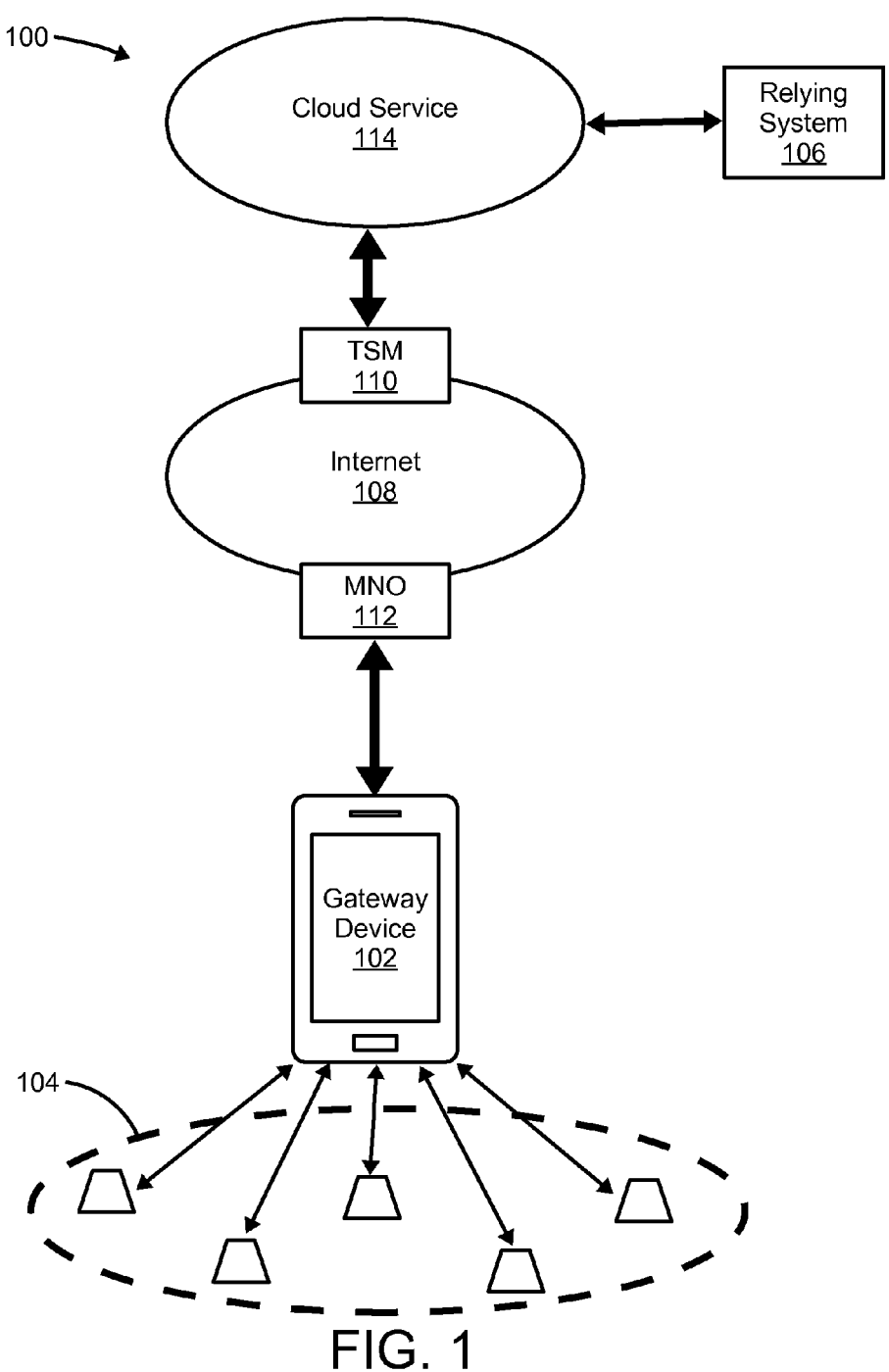
FIG. 1 illustrates a system for securely obtaining health information according to the disclosure.

FIG. 1 illustrates a system 100 for securely obtaining health information according to the disclosure. A gateway device (GD) 102 is in wireless communication with one or more personal medical devices (PMDs) 104. The GD 102 is in wired or wireless communication via the Internet 108 or other network service with a relying system (RS) 106. The RS 106 may be a health service provider, a doctor, or other party that is allowed access to the information gathered from or sent to the PMDs 104. Information exchanged by the RS 106 with the PMDs 104 via the GD 102 may be stored in a cloud service 114 to which the RS 106 and GD 102 have shared access. It is important that the RS 106 be able to verify the authenticity of data from the PMDs 104 that the RS 106 receives from the GD 102. Communication between the RS 108 and the GD 102 may be via a trusted service manager (TSM) 110, a mobile network operator (MNO) 112, or other service providing secure communications between the RS 106 and a secure area in the GD 102.

The GD 102 may be a smart phone, a tablet, a laptop, or other suitable portable processing device. A processor of the GD 102 includes a secure area such as a trusted execution environment (TEE) or other system that provides services such as protection with respect to confidentiality and integrity of code and data loaded therein, isolated execution of applications, isolation of hardware from non-secure applications, and integrity of applications and confidentiality of their data.

The PMDs 104 may be sensors for reporting on the heart rate, blood pressure, blood sugar level, or other measurable characteristic of a user's body. The PMDs 104 may also be actuators for dispensing insulin, electrical stimulation, or other therapeutic action. A PMD may also be referred to as an eHealth device. A PMD may include a health sensor/actuator application that uses a sensor/actuator driver, a hardware security module, and a communication module to provide its functionality in cooperation with an external device. A PMD typically has little or no direct user interface functionality, relying, instead on the external device for such functionality.

As is discussed in greater detail below, the RS 106 is configured to load a gateway application into the GD 102, typically via the TSM 110 or the MNO 112. The gateway application is executed in a secure area of the GD 102. The gateway application provides local control of the PMDs 104, using one or more protocols and security policies set by the RS 106.

Figure 2:
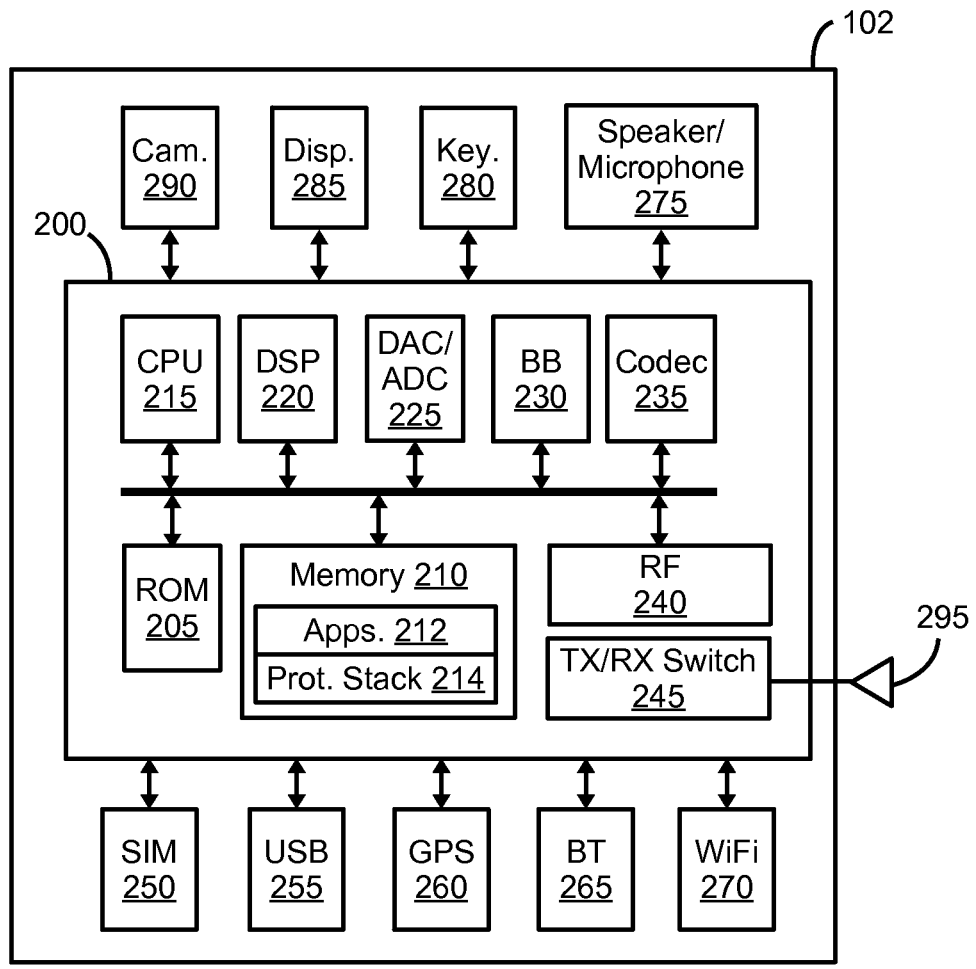
FIG. 2 illustrates a gateway device according to the disclosure.

FIG. 2 illustrates the gateway device 102 according to the disclosure. The GD 102 may be a mobile phone, tablet, laptop, or other suitable portable device. The GD 102 includes a secure area suitable for executing a gateway application according to the disclosure. The GD 102 comprises core circuitry 200, which includes read-only memory (ROM) 205, random access memory (RAM) 210, central processing unit (CPU) 215, digital signal processor (DSP) 220, digital-to-analog converter (DAC)/analog-to-digital converter (ADC) circuitry 225, baseband (BB) circuitry block 230, codec circuitry block 235, radio frequency (RF) circuitry block 240, transmit (TX)/receive (RX) switch 245, and antenna 295.

In one embodiment, ROM 205 may store a boot-routine and other static data and RAM 210 may store an operating system (not shown), applications 212, and protocol stack 214. The ROM 205 and RAM 210 include a trusted execution environment or other secure area in which the confidentiality and integrity of code and data may be ensured. In an advantageous embodiment, ROM 205 and RAM 210 may comprise a single electronically erasable memory, such as a Flash memory, that is used in conjunction with a conventional RAM memory that is used to store dynamic data.

The GD 102 further comprises SIM card interface 250, USB interface 255, GPS receiver 260, Bluetooth (BT) transceiver 265, WiFi (or WLAN) transceiver 270, speaker and microphone circuitry block 275, keyboard 280, display 285, and camera 290. In some embodiment, keyboard 280 and display 285 may be implemented together as a touch screen display.

CPU 215 is responsible for the overall operation of GD 210. In an exemplary embodiment, CPU 215 executes applications 212 and protocol stack 214. CPU 215 runs the application layer and a wide variety of applications may be run in a smart phone implementation. Applications 212 may include audio, video, and image/graphics applications. CPU 215 may run applications 212 that support various audio formats such as MP3, MP4, WAV, and rm. CPU 215 may run image applications 212 that support JPEG image formats and video applications 212 that support video formats (e.g., MPEG-1 to MPEG-5). CPU 215 may support various operating systems (not shown), such as Symbian, java, android, RT-Linux, Palm, and the like. For time critical applications, CPU 215 runs a real-time operating system (RTOS). In addition to the physical layer, there are other layers, including protocol stack 214, that enable GD 102 to work with a network base station. In an exemplary embodiment, protocol stack 214 is ported on CPU 215.

DAC/ADC circuitry block 225 converts analog speech signals to digital signals, and vice versa, in GD 210. In the transmit path, the ADC-converted digital signal is sent to a speech coder. Various types of ADCs are available, including sigma delta type. Automatic gain control (AGC) and automatic frequency control (AFC) are used in the receive path to control gain and frequency. AGC helps maintain satisfactory DAC performance by keepings signals within the dynamic range of the DAC circuits. AFC keeps frequency error within limit to achieve better receiver performance.

Baseband (BB) circuitry block 230 may be implemented as part of DSP 220, which executes many of the baseband processing functions (i.e., physical layer, Layer 1, or L1 functions). BB circuitry block 230 may be ported on DSP 220 to meet the latency and power requirements of GD 210. BB circuitry block 230 converts voice and data to be carried over the air interface to I/Q baseband signals.

BB circuitry block 230 may change from modem to modem for various air interface standards, such as GSM, CDMA, Wimax, LTE, HSPA, and others. BB circuitry block 230 is often referred to as the physical layer, or Layer 1, or L1. For mobile phones that work on GSM networks, the baseband part (Layer 1) running on DSP 220 and the protocol stack 214 running on CPU 215 are based on the GSM standard. For CDMA mobile phones, the Layer 1 and protocol stack 214 are based on the CDMA standard, and so on, for the LTE and HSPA standards-based mobile phones.

For speech or audio inputs, codec circuitry block 235 may compress and decompress the signal to match the data rate to the frame in which the data is sent. By way of example, codec circuitry block 235 may convert speech at an 8 KHz sampling rate to a 13 kbps rate for a full rate speech traffic channel. To do this, a residually excited linear predictive coder (RELP) speech coder may be which compresses 260 bits into a 20 ms. duration to achieve a 13 kbps rate.

The baseband or physical layer adds redundant bits to enable error detection as well as error correction. Error detection may be obtained with CRC and error correction using forward error correction techniques, such as a convolutional encoder (used in transmitter path) and a viterbi decoder (used in receive path). Interleaving may be done for the data, which helps in spreading the error over time, thereby helping the receiver de-interleave and decode the frame correctly.

RF circuitry block 240 includes an RF up-converter and an RF down-converter. For a GSM system, the RF up-converter converts modulated baseband signals (I and Q) either at zero intermediate frequency (IF) or some IF to RF frequency (890-915 MHz). The RF down-converter converts RF signals (935 to 960 MHz) to baseband signals (I and Q). For a GSM system, GMSK modulation is used.

Antenna 295 is a metallic object that converts and electromagnetic signal to and electric signal and vice versa. Commonly used antennas may include a helix type, a planar inverted F-type, a whip, or a patch type. Microstrip patch type antennas are popular among mobile phones due to small size, easy integration on a printed circuit board and multi-frequency band of operation. In a preferred embodiment of GD 210, antenna 295 may support different wire-area standards, including GSM, CDMA, LTE, and WiMAX, as well as short-range standards, including WiFi (WLAN), Bluetooth, and so on.

If antenna 295 comprises only one antenna used for both transmit and receive operations at different times, the TX/RX switch 245 couples both the transmit (TX) path and the receive (RX) path to antenna 295 at different times. TX/RS switch 245 is controlled automatically by DSP 220 based on a GSM frame structure with respect to the physical slot allocated for that particular GSM mobile phone in both the downlink and the uplink. For frequency division duplexing (FDD) systems, TX/RX switch 245 may be implement as a diplexer that acts as filter to separate various frequency bands.

The GD 102 provides connectivity with laptops or other devices using WiFi (or WLAN) transceiver 270, BT transceiver 265, and universal serial bus (USB) interface 255. The GD 102 also uses GPS receiver 260 in applications 212 that require position information. If GD 102 is a conventional smart phone, applications 212 may include many popular applications, such as Facebook, Twitter, a browser, and numerous games that come pre-installed with GD 210.

Speaker and microphone circuitry block 275 comprises microphone circuitry (or mic) that converts acoustic energy (i.e., air pressure changes caused by speech or other sounds) to electrical signals for subsequent processing. Speaker and microphone 275 further comprises speaker circuitry that converts an electrical audio signal to an audible signal (pressure changes) for human hearing. The speaker circuitry may include an audio amplifier to get required amplification of the audio signal and may further include a volume control circuit to change (increase or decrease) the amplitude of the audio signal.

The GD 102 preferably includes camera 290. Presently, almost all mobile phones feature a camera module. Camera 290 may comprise a 12 megapixel, 14 megapixel, or even a 41 megapixel camera.

Display 285 may comprise, by way of example, a liquid crystal display (LCD), a thin-film transistor (TFT) screen, and organic light emitting diode (OLED) display, a thin film diode (TFD) display, or a touch screen of capacitive and resistive type.

In a simple embodiment, keypad 280 may comprise a simple matrix type keypad that contains numeric digits (0 to 9), alphabetic characters (A to Z), special characters, and specific function keys. In a more advanced embodiment for a smart phone implementation, keypad 280 may be implemented in the mobile phone software, so that keyboard 280 appears on display 285 and is operated by the user using the touch of a finger tip.

BB circuitry block 230, RF circuitry block 240, TX/RX switch 245, WiFi (or WLAN) transceiver 270, BT transceiver 265, and USB interface 255 comprise a communications interface that enables the gateway device 102 to communicate either wired or wirelessly with PMDs 104 and RS 106.

According to the principles of the disclosure, applications 212 include a gateway application for managing one or more personal medical devices and providing secure communication with the personal medical devices and a relying system such as a health service provider.

Figure 3:
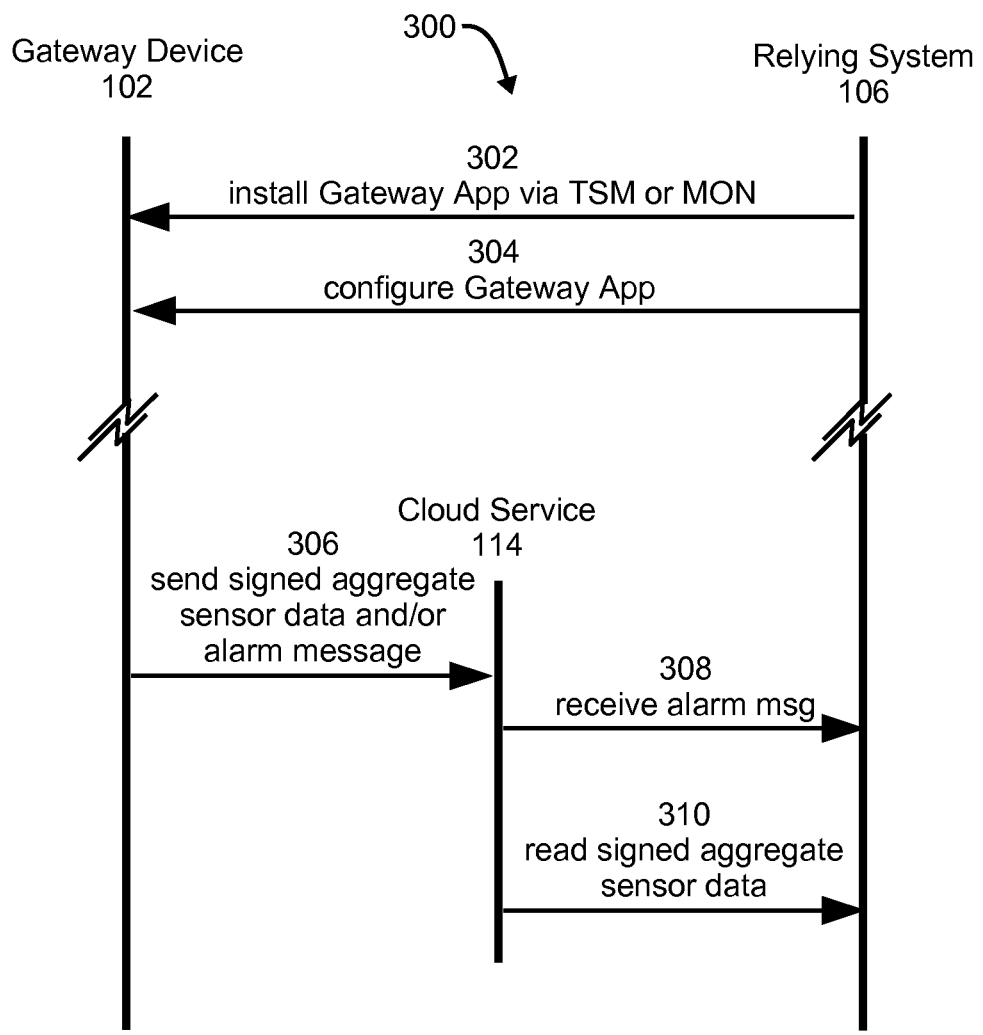
FIG. 3 presents a sequence diagram illustrating a method of securely obtaining health information according to the disclosure.

FIG. 3 presents a sequence diagram 300 illustrating a method of securely obtaining health information according to the disclosure. In step 302, the RS 106 uses a trusted service manager, which may be provided by a third party or a mobile network operator, to securely install gateway application in the secure execution environment of the gateway device 102. In step 304, the RS 106 configures the gateway application with a digital certificate, relevant metadata, and a security policy administered by the relying system for the gateway application to implement relating at least to communications with the PMDs 104 and the RS 106. The RS 106 implicitly trusts the gateway application once it is successfully installed and updates the gateway application and/or security policy if a security breach is later identified.

Relevant metadata may include, but is not limited to, cryptographic parameters; URLs of PMD manufacturers, which may be used to update firmware of installed PMDs; firmware signatures of one or more installed PMDs, which may be used to check the integrity and authenticity of PMD firmware; and anti-virus software and signature databases, which may be used to protect PMDs from viruses.

As is discussed in greater detail below, once installed and executing, the gateway application establishes secure communication with the PMDs 104 and begins collecting data from PMD sensors—enforcing relevant elements of the security policy received from the RS 106 in step 304. At a subsequent point in time, in step 306, the gateway application aggregates information collected from the PMD sensors, signs the packet of aggregated information with its private key, and sends the signed aggregated sensor data as a message to the RS 106. The message may be stored into a shared storage space in cloud service 114 or may be sent directly to the RS 106.

Such aggregated information from the PMDs may be sent by the gateway application to the RS 106 on a periodic basis, or may be sent when a triggering event occurs. Examples of such a triggering event include but are not limited to collection of a threshold number of measurements, or a measurement having a threshold value (for example, blood pressure below a certain level). Such triggering events may additionally or alternatively cause the gateway application to generate an alarm message having content relating to the triggering action, sign the alarm message with its private key, and send the signed alarm message to the RS 106.

In step 308, the RS 106 receives a signed alarm message via the cloud service 114 (or directly from the GD 102), authenticates the alarm message using the public key of the gateway application from which the message purports to come, and then takes an associated specified action. Examples of such specified actions include but are not limited to notifying a physician, or instructing an action by a PMD actuator associated with the patient associated with the alarm condition. In step 310, the RS 106 reads one or more signed packets of aggregated sensor information, authenticates the packets using the public key of the gateway application from which the packets purport to come, and then uses the aggregated information for purposes specified by the doctor or other health service provider using the RS 106. The RS 106 may already have the public key of the gateway application, or the RS 106 may receive the public key from the gateway application after it has been installed and initialized. If the gateway application is running in a TEE, the RS 106 may use the TEE application programming interface to instruct the gateway application to generate a new public/private key pair for subsequent use in communications with the RS 106.

Figure 4:
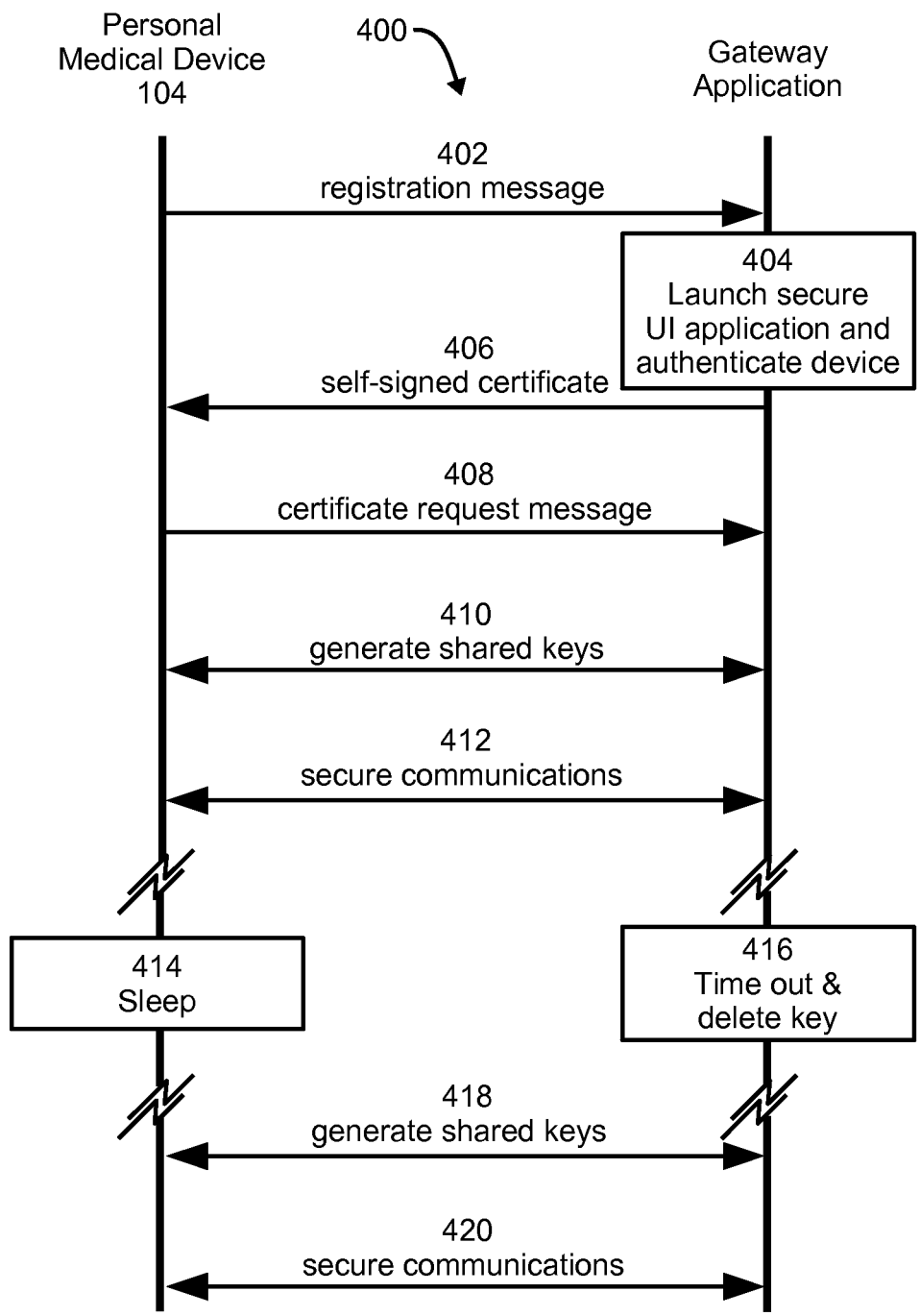
FIG. 4 presents a sequence diagram illustrating a method of managing data collection from a personal medical device according to the disclosure.

FIG. 4 presents a sequence diagram 400 illustrating a method of managing data collection from a personal medical device according to the disclosure. In step 402, one of the PMDs 104 sends out a registration message, which may include authentication information including but not limited to model number, manufacturer identifier, and serial number. Such a registration message maybe sent by the PMD 104 upon initial power up or when communication with a gateway device has been lost. In the scenario presented in diagram 400, the gateway device 102 happens to be within communication range of the PMD 104, and the registration message is received by the gateway application executing in the gateway device 102.

In step 404, the gateway application launches a secure user interface (UI) application, presents authentication information received from the PMD 104 to a user of the gateway device 102, and asks the user to verify the information and authenticate himself/herself to the gateway application. Such authentication or user presence verification can be achieved using a user personal identification number (PIN) or biometric authentication (such as a fingerprint scan on a sensor of the gateway device 102). In this way, an authorized user gives the go-ahead for registration of a PMD by authenticating himself/herself to the gateway application.

Once the user is authenticated to the gateway application, in step 406, the gateway application sends a self-signed digital certificate to the requesting PMD 104. In step 408, the PMD 104 sends a certificate request message containing its public key and other relevant information to the gateway application.

In step 410, the gateway application sends the PMD 104 a certificate signed with the public key of the PMD 104, and the gateway application and the PMD 104 exchange secure messages to generate a shared session key (or keys) for use in step 412 in subsequent secure communication between the gateway application and the PMD 104.

Typically, the PMD 104, after a short period of inactivity, will enter a sleep mode in step 414, to preserve the charge on its battery or other power source. In step 416, the gateway application determines that the PMD 104 has entered sleep mode and deletes the shared key currently being used to communicate with the PMD 104. Typically, the gateway application makes this determination upon the expiration of an activity timeout timer. In other embodiments, the gateway application may receive a message from the PMD 104 that includes an indication that the PMD 104 is about to enter sleep mode.

When the PMD 104 exits sleep mode, in step 418, it engages again in an exchange of secure messages to generate a new shared session key (or keys) for use in step 420 in secure communication between the gateway application and the PMD 104. Through the use of shared keys in both steps 412 and 420, the gateway application can ensure the authenticity and integrity of health sensor information received from a PMD. Because the gateway application can guarantee the information's authenticity and integrity—and because the information packets sent from the gateway application to the relying system 106 are signed with the gateway application's private key—the doctor or other health service provider using the relying system 106 can rely upon the authenticity and integrity of PMD information received from the system according to the disclosure.

Additionally, in embodiments where the gateway application is running in a TEE provided by the GD 102, the relying system 106 can use the TEE's API to ask the gateway application to generate a new public/private key and cause the gateway application to regenerate shared key(s) with each PMD 104 using the new gateway application public/private key.

In some embodiments, the gateway application uses the information received from the PMD 104 relating to manufacturer and model number of the PMD 104 to periodically access via the Internet 108 a website providing firmware updates for PMDs produced by the manufacturer. The gateway application may determine a version number of firmware currently in use by a PMD 104 from information received from the PMD 104. If a newer version of the firmware is available from the manufacturer's website, the gateway application may download the new firmware and load it into the PMD 104. Once the PMD 104 is restarted and executing the new firmware, some or all of the steps of diagram 400 may be repeated to reestablish secure communications between the gateway device 102 and the PMD 104.

In still other embodiments, the gateway application loads from the PMD 104 its current firmware and analyzes the firmware to detect whether a hacker, virus program, or other unauthorized entity has made unauthorized changes to the firmware. If such changes are detected, the gateway application may notify a user of the GD 102 and/or a user of the RS 106 that the unauthorized changes have been made. Additionally or alternatively, the gateway application may eradicate the unauthorized changes by reloading the PMD 104 with authorized firmware obtained from the PMD manufacturer.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A gateway device comprising:
 a memory;
 a communications interface configured to receive a gateway application from a relying system (RS): and
 a hardware processor coupled to the memory and the communications interface and configured to execute the gateway application in a secure area of the hardware processor and the memory, wherein the gateway application is configured to cause the hardware processor to:
 establish a first secure communications link with a personal medical device (PMD) by exchanging one or more security certificates with the PMD, wherein the one or more security certificates includes a self-signed certificate;
 establish a second secure communications with the RS;
 receive information from the PMD via the first secure communications link; and
 send aggregated received information to the RS via the second secure communications link.

2. The gateway device of claim 1, further configured to communicate with the RS via a trusted service manager.

3. The gateway device of claim 1, wherein the gateway application is further configured to establish the first secure communications link with the PMD by authenticating a user of the gateway application.

4. The gateway device of claim 3, wherein the gateway application is further configured to:
 exchange first information with the PMD to generate a first session key for use in the first secure communications link between the gateway device and the PMD;
 determine that the PMD has entered a sleep mode; and
 prior to further communications with the PMD, exchange second information with the PMD to generate a second session key for use in the first secure communications link between the gateway device and the PMD.

5. The gateway device of claim 3, wherein the gateway application is further configured to issue the at least one security certificate to the PMD.

6. The gateway device of claim 1, wherein the gateway application is further configured to sign aggregated received information sent to the RS with a private key.

7. The gateway device of claim 1, wherein the gateway application is further configured to:
 receive firmware for use in the PMD; and
 download the firmware to the PMD via the first secure communications link with the PMD.

8. A system for securely obtaining health information from a personal medical device, the system comprising:
   a server configured to install a gateway application (GA) in a gateway device (GD), the GA configured to, when executed by a hardware processor in a secure area of the GD, cause the GD to;
   establish a first secure communications link with a personal medical device (PMD) by exchanging at least one security certificate between the GD and the PMD, wherein the one or more security certificates includes a self-signed certificate; and
   receive information from the PMD via the first secure communications link; and
   aggregate information received from the PMD, wherein the server is configured to receive the aggregated information from the GD via a second secure communications link.

9. The system of claim 8, further configured to communicate with the GD via one of a trusted service manager and a mobile network operator.

10. The system of claim 8, wherein the gateway application is further configured to establish the first secure communications link with the PMD by authenticating a user of the gateway application to the PMD.

11. The system of claim 10, wherein the gateway application is further configured to: exchange first information with the PMD to generate a first session key for use in the first secure communications link between the gateway device and the PMD;
   determine that the PMD has entered a sleep mode; and
   prior to further communications with the PMD, exchange second information with the PMD to generate a new session key for use in the subsequent secure communications between the gateway device and the PMD.

12. The system of claim 8, wherein:
   the GA is further configured to sign the aggregated information with a private key; and
   the system is further configured to confirm that received aggregated information from the GA is signed with the GA's private key.

13. A method of managing secure data collection from a personal medical device (PMD), the method comprising:
   receiving, at a gateway device (GD) from a relying system (RS), a gateway application (GA);
   executing the gateway application by a hardware processor in a secure area of the gateway device (GD) to establish a first secure communications link between the GA and the PMD by exchanging at least one security certificate with the PMD, wherein the one or more security certificates includes a self-signed certificate;
   establishing a second the secure communications link between the GA and the RS;
   receiving information from the PMD via the first secure communications link; and
   sending aggregated received information to the RS via the second secure communications link.

14. The method of claim 13, wherein the GA is received from the RS via a trusted service manager.

15. The method of claim 13, wherein establishing the first secure communications with the PMD includes authenticating a user of the gateway application to the PMD.

16. The method of claim 15, further comprising:
   exchanging first information with the PMD to generate a first session key for use in the first secure communications link between the gateway device and the PMD;
   determining that the PMD has entered a sleep mode; and
   prior to further communications with the PMD, exchanging second information with the PMD to generate a second session key for use in the first secure communications link between the gateway device and the PMD.

17. The method of claim 13, wherein sending aggregated received information to the RS includes signing the aggregated received information with a private key.

18. The method of claim 13, further comprising: receiving firmware for use in the PMD; and
   downloading the firmware to the PMD via the first secure communications link with the PMD.

19. The method of claim 13, further comprising: receiving firmware from the PMD; and
   analyze the firmware to detect changes to the firmware.

20. The method of claim 19, further comprising at least one of:
   notifying a user of the GD of the presence of the changes to the firmware,
   notifying a user of the RS of the presence of the changes to the firmware, and downloading authorized firmware to the PMD via the first secure communications link with the PMD.

* * * * *